(12) United States Patent
Slavin

(10) Patent No.: US 10,058,249 B2
(45) Date of Patent: Aug. 28, 2018

(54) METHOD, APPARATUS, AND ARTICLE FOR OPTIMIZED MYOCARDIAL T1 MAPPING

(71) Applicant: General Electric Company, Schenectady, NY (US)

(72) Inventor: Glenn Scott Slavin, Silver Spring, MD (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 516 days.

(21) Appl. No.: 14/325,958

(22) Filed: Jul. 8, 2014

(65) Prior Publication Data

US 2016/0007853 A1 Jan. 14, 2016

(51) Int. Cl.
| | |
|---|---|
| *G01R 33/56* | (2006.01) |
| *G01R 33/567* | (2006.01) |
| *G01R 33/50* | (2006.01) |
| *A61B 5/00* | (2006.01) |
| *A61B 5/04* | (2006.01) |
| *A61B 5/0456* | (2006.01) |
| *A61B 5/055* | (2006.01) |
| *G01R 33/561* | (2006.01) |

(52) U.S. Cl.
CPC ........ *A61B 5/0044* (2013.01); *A61B 5/04012* (2013.01); *G01R 33/50* (2013.01); *G01R 33/5673* (2013.01); *A61B 5/0456* (2013.01); *A61B 5/055* (2013.01); *A61B 5/7292* (2013.01); *G01R 33/5614* (2013.01)

(58) Field of Classification Search
None
See application file for complete search history.

(56) References Cited

U.S. PATENT DOCUMENTS

2011/0137146 A1* 6/2011 Edelman ............ G01R 33/5635
600/410

OTHER PUBLICATIONS

Hwang et al. 2013 Korean Circulation J. 43:1-6.*
Song et al. 2012 Magnetic Resonance in Medicine 67:622-627.*
Chow et al. 2014 Magnetic Resonance in Medicine 71:2082-2095.*
Slavin et al. 2013 J. Cardiovasc. Mag. Reson. 15(Supp. 1):P3 3 pages.*
Scheffler et al. 2003 Eur. Radiol. 13:2409-2418.*
Blume, et al.; Interleaved T1 and T2 Relaxation Time Mapping for Cardiac Applications; Journal of Magnetic Resonance Imaging (2009).
Chow et al.; Saturation Recovery Single-Shot Acquisition (SASHA) for Myocardial T1 Mapping; Magnetic Resonance in Medicine (2014).
Deichmann, et al.; Quantification of T1 Values by Snapshot-Flash NMR Imaging; Journal of Magnetic Resonance (1992).
Goldfarb; Quantitative Breath-Hold Monitoring of Myocardial Gadolinium Enhancement Using Inversion Recovery TrueFISP; Magnetic Resonance in Medicine (2005).

(Continued)

*Primary Examiner* — Tse Chen
*Assistant Examiner* — Patrick M Mehl
(74) *Attorney, Agent, or Firm* — Grogan, Tuccillo & Vanderleeden, LLP

(57) ABSTRACT

A method for mapping T1 in myocardium includes selecting a recovery delay from EKG signal data; imposing a saturation pulse on the myocardium; waiting the recovery delay; and acquiring bSSFP data after the recovery delay.

22 Claims, 5 Drawing Sheets

(56) References Cited

OTHER PUBLICATIONS

Iles, et al.; Evaluation of Diffuse Myocardial Fibrosis in Heart Failure with Cardiac Magnetic Resonance Contrast-Enhanced T1 Mapping; Journal of the American College of Cardiology (2008).
Messroghli; Modified Look-Locker Inversion Recovery (MOLLI) for High-Resolution T1 Mapping of the Heart; Magnetic Resonance in Medicine (2004).
Piechnik; Shortened Modified Look-Locker Inversion recovery (ShMOLLI) for clinical myocardial T1-mapping at 1.5 and 3 T within a 9 heartbeat breathhold; Journal of Cardiovascular Magnetic Resonance (2010).
Schmitt, et al.; Inversion Recovery TrueFISP: Quantification of T1, T2, and Spin Density; Magnetic Resonance in Medicine (2004).
Stainsby, et al.; Comparing the accuracy and precision of SMART1Map, SASHA and MOLLI; Journal of Cardiovascular Magnetic Resonance; (2014).

\* cited by examiner

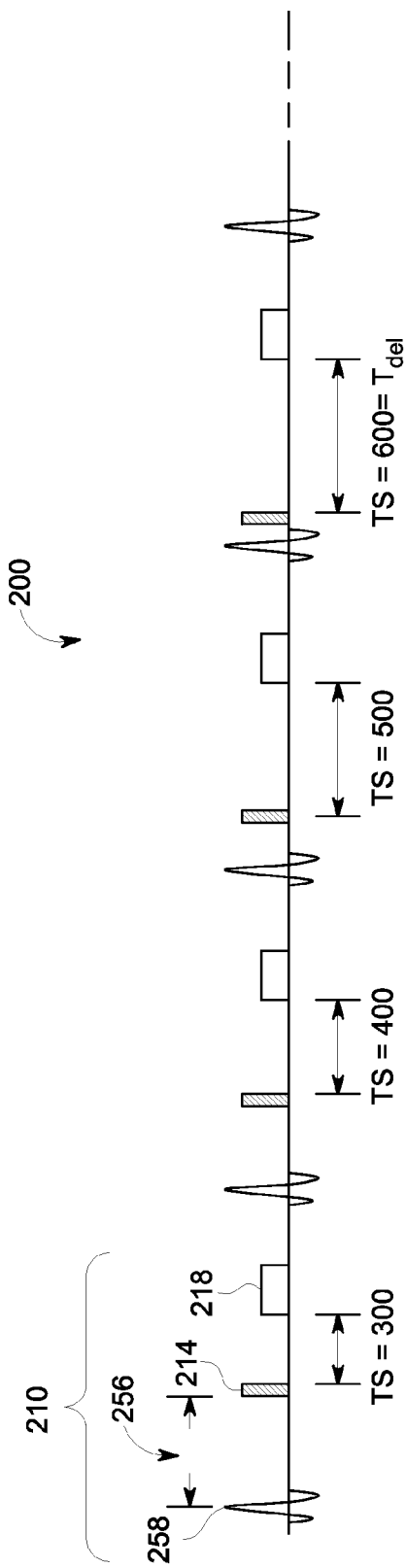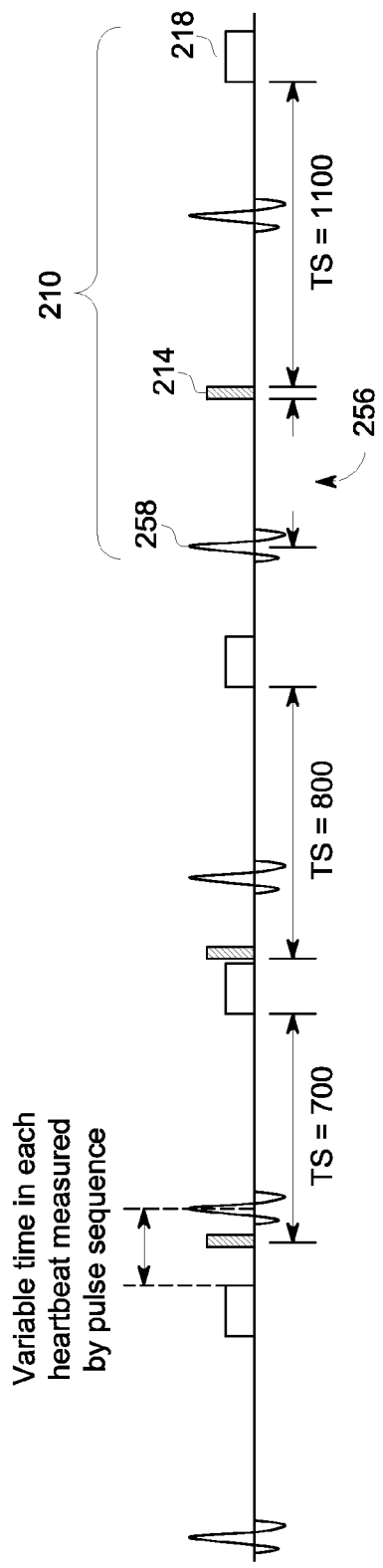

METHOD, APPARATUS, AND ARTICLE FOR OPTIMIZED MYOCARDIAL T1 MAPPING

BACKGROUND

Technical Field

Embodiments of the invention relate generally to magnetic resonance imaging (MRI). Particular embodiments relate to cardiac MRI.

Discussion of Art

In MRI imaging, when human or other animal tissue is subjected to a uniform magnetic field, i.e., a polarizing field B0, the individual magnetic moments of particle spins in the tissue attempt to align with the polarizing field, but precess about the field in random order at their characteristic Larmor frequency. If the tissue is subjected to an RF magnetic field, i.e., excitation field B1, which defines an x-y plane and varies at a frequency near a Larmor frequency of selected particles, the net aligned moment, or "longitudinal magnetization" of those selected particles, may be rotated, or "tipped", into the x-y plane to produce a net transverse magnetic moment. After B1 is terminated, the tipped spins "relax" back into the precession defined by B0, and, as a result, produce RF signals. Some of the relaxation RF signals vary in amplitude according to an exponential function that is characterized by a recovery time T1. T1 varies according to chemical properties of the imaged tissue. Therefore, it is possible to characterize tissue by quantifying its T1.

For cardiac applications, T1 quantification has been demonstrated as a non-invasive means for quantifying acute and chronic myocardial infarction, diffuse fibrosis, heart failure, and myocardial amyloidosis. Although T1-weighted imaging, such as myocardial-delayed enhancement (MDE), is part of routine clinical cardiac MR, an inappropriate selection of the inversion time in these methods can potentially result in poor contrast between normal and abnormal myocardium. Furthermore, quantitative analysis of T1-weighted images, such as for infarct sizing and gray zone characterization, are limited by the qualitative signal intensity variations in individual images. In comparison, T1 mapping can overcome these potential limitations and provide the underlying quantitative tissue property of the different types of normal and abnormal myocardium.

A number of approaches have recently been proposed for characterizing the physical properties of myocardium directly through T1 measurement, rather than indirectly through T1-weighted imaging. None of these approaches, however, has achieved objectively accurate results in a breath-hold acquisition. Additionally, systolic imaging has proven difficult due to challenges in providing a saturation pulse trigger delay that is short enough to permit imposing an adequate saturation pulse and recovering adequate saturation data in the short time between an R-wave trigger and the subsequent systole. With reference to EKG signal data, an R-wave is the middle and positive-going portion of a normal QRS wave within the EKG signal data; the QRS wave precedes ventricular systole.

In view of the above, it is desirable to accurately, robustly, and reproducibly quantify myocardial T1, so that images can be compared objectively between patients as well as between scanners and sites. Additionally, it is desirable to acquire a sufficient number of data points along a sufficient duration of the recovery curve to allow reliable curve fitting under any clinical imaging situation. Moreover, it is desirable to obtain adequate saturation recovery data to permit T1 mapping during cardiac systole.

BRIEF DESCRIPTION

In embodiments, a method for mapping T1 in myocardium includes selecting a recovery delay from EKG signal data; imposing a saturation pulse on the myocardium; waiting the recovery delay; and acquiring bSSFP data after the recovery delay.

Other embodiments provide an MRI system configured for mapping of myocardial T1 in a patient. The inventive MRI system includes a magnet assembly; a physiological acquisition controller configured for connection to the patient; and an MRI controller coupled to the physiological acquisition controller for receiving data that includes EKG signal data, and coupled to the magnet assembly for implementing an MRI pulse sequence. The MRI controller is configured to select a recovery delay based at least on the EKG signal data, impose a saturation pulse on the patient's myocardium via the magnet assembly, wait the recovery delay, and acquire bSSFP data after the recovery delay.

In other embodiments, an article of computer-readable media is encoded with at least one bSSFP data point, or a T1 recovery curve, that was obtained according to a process comprising selecting a recovery delay based at least on EKG signal data; imposing a saturation pulse on the myocardium; waiting the recovery delay; and acquiring bSSFP data after the recovery delay.

DRAWINGS

The present invention will be better understood from reading the following description of non-limiting embodiments, with reference to the attached drawings, wherein below:

FIGS. 4A-4D show graphically a pulse sequence according to the method of FIG. 2.

DETAILED DESCRIPTION

Figure 1:
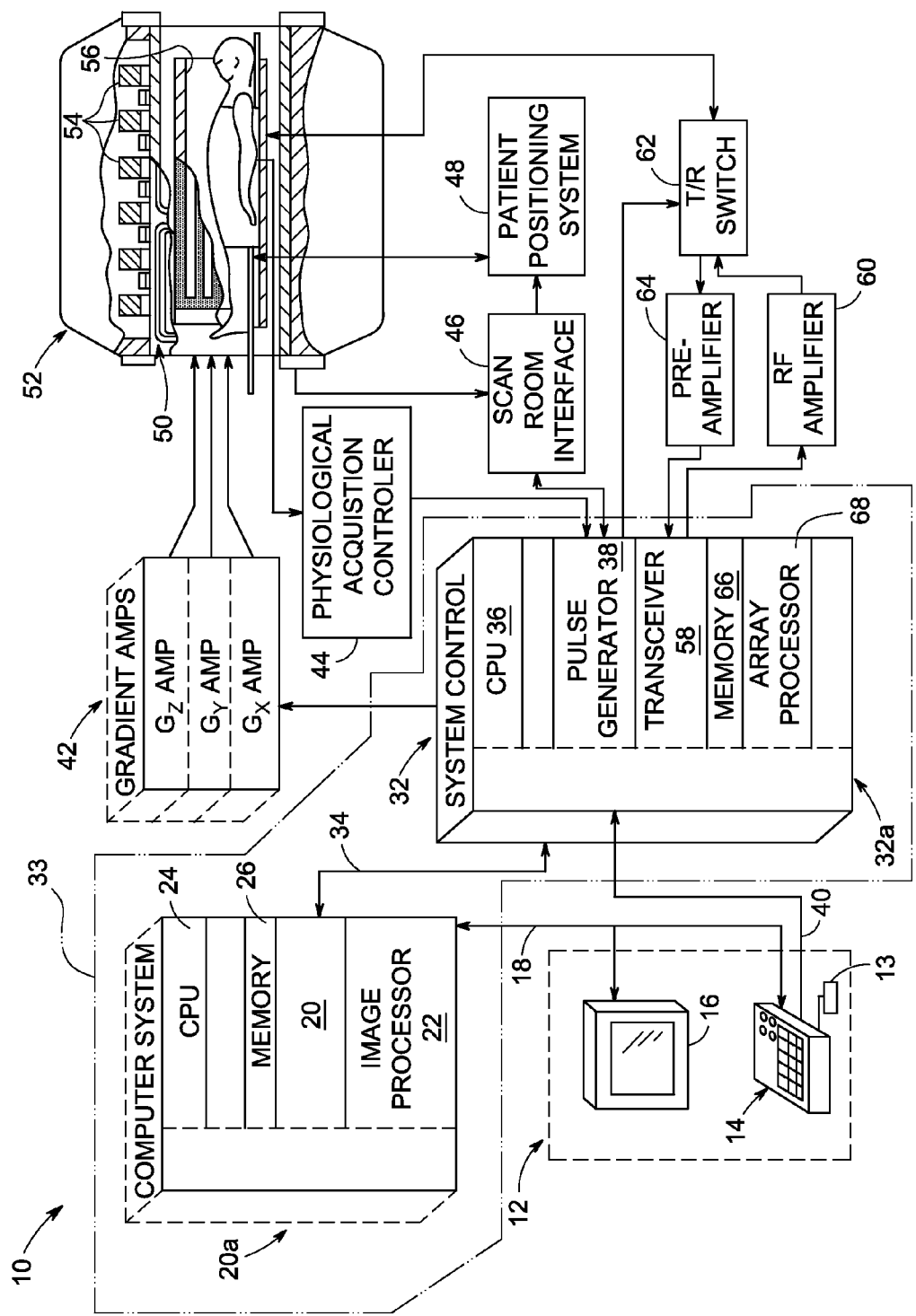
FIG. 1 shows schematically an MRI system in which embodiments of the invention are implemented.

Reference will be made below in detail to exemplary embodiments of the invention, examples of which are illustrated in the accompanying drawings. Wherever possible, the same reference characters used throughout the drawings refer to the same or like parts, without duplicative description. Aspects of the invention relate to pulse sequences used for MRI. Exemplary embodiments of the present invention are described with respect to cardiac T1 mapping.

FIG. 1 shows major components of an exemplary magnetic resonance imaging (MRI) system 10 that incorporates embodiments of the present invention. The operation of the system is controlled from an operator console 12, which includes a keyboard or other input device 13, a control panel 14, and a display screen 16. The input device 13 can include a mouse, joystick, keyboard, track ball, touch activated screen, light wand, voice control, or any similar or equivalent input device, and may be used for interactive geometry prescription. The console 12 communicates through a link 18 with a separate computer system 20 that enables an operator to control the production and display of images on the display screen 16. The computer system 20 includes a number of modules that communicate with each other through a backplane 20a. The modules of the computer system 20 include an image processor module 22, a CPU module 24 and a memory module 26 that may include a frame buffer for storing image data arrays. The computer system 20 is linked to archival media devices, permanent or back-up memory storage or a network for storage of image data and programs, and communicates with a separate system control 32 through a high-speed signal link 34. The computer system 20 and the system control 32 collectively form an "MRI controller" 33. According to embodiments and aspects of the invention, the MRI controller 33 is configured to accomplish 3-D multispectral MRI with enhanced T1 contrast, according to algorithms further discussed below.

The system control 32 includes a set of modules connected together by a backplane 32a. These include a CPU module 36 as well as a pulse generator module 38. The CPU module 36 connects to the operator console 12 through a serial link 40. It is through link 40 that the system control 32 receives commands from the operator to indicate the scan sequence that is to be performed. The CPU module 36 operates the system components to carry out the desired scan sequence and produces data which indicates the timing, strength and shape of the RF pulses produced, and the timing and length of the data acquisition window. The CPU module 36 connects to several components that are operated by the MRI controller 33, including the pulse generator module 38 (which controls a gradient amplifier 42, further discussed below), a physiological acquisition controller ("PAC") 44, and a scan room interface circuit 46.

The CPU module 36 receives patient data from the physiological acquisition controller 44, which receives signals from a number of different sensors connected to the patient, such as ECG signals from electrodes attached to the patient. And finally, the CPU module 36 receives from the scan room interface circuit 46, signals from various sensors associated with the condition of the patient and the magnet system. It is also through the scan room interface circuit 46 that the MRI controller 33 commands a patient positioning system 48 to move the patient or client C to a desired position for the scan.

The pulse generator module 38 operates the gradient amplifiers 42 to achieve desired timing and shape of the gradient pulses that are produced during the scan. The gradient waveforms produced by the pulse generator module 38 are applied to the gradient amplifier system 42 having Gx, Gy, and Gz amplifiers. Each gradient amplifier excites a corresponding physical gradient coil in a gradient coil assembly, generally designated 50, to produce the magnetic field gradients used for spatially encoding acquired signals. The gradient coil assembly 50 forms part of a magnet assembly 52, which also includes a polarizing magnet 54 and a whole-body RF coil 56. In an embodiment of the invention, RF coil 56 is a multi-channel coil. A transceiver module 58 in the system control 32 produces pulses that are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 32 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either transmit mode or receive mode.

After the multi-channel RF coil 56 picks up the RF signals produced from excitation of the target, the transceiver module 58 digitizes these signals. The MRI controller 33 then processes the digitized signals by Fourier transform to produce k-space data, which then is transferred to a memory module 66, or other computer readable media, via the system control 32. "Computer readable media" may include, for example, structures configured so that electrical, optical, or magnetic states may be fixed in a manner perceptible and reproducible by a conventional computer: e.g., text or images printed to paper or displayed on a screen, optical discs, or other optical storage media; "flash" memory, EEPROM, SDRAM, or other electrical storage media; floppy or other magnetic discs, magnetic tape, or other magnetic storage media.

A scan is complete when an array of raw k-space data has been acquired in the computer readable media 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory. In response to commands received from the operator console 12, this image data may be archived in long-term storage or it may be further processed by the image processor 22 and conveyed to the operator console 12 and presented on the display 16.

Figure 2:
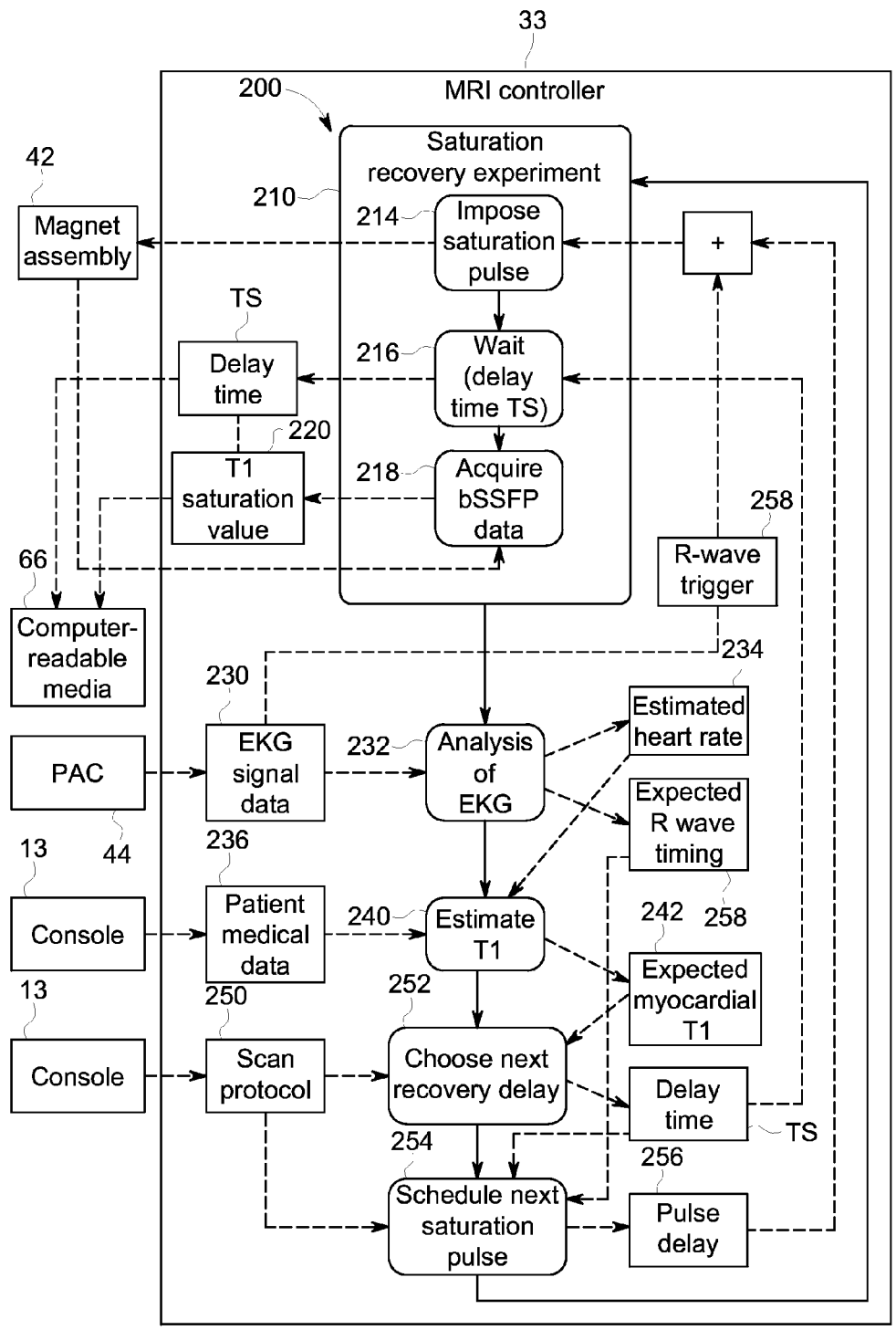
FIG. 2 shows schematically a pulse sequence method for mapping T1 in myocardium, according to a first embodiment of the invention.

Referring to FIG. 2, according to embodiments of the invention, the MRI controller 33 implements a pulse sequence 200. The pulse sequence 200 comprises repeated saturation recovery experiments 210 that produce a set of images with T1 saturation values 220 corresponding to a set of recovery delays TS. Each experiment 210 includes imposing a saturation pulse 214 (e.g., a non-slice-selective pulse), waiting 216 for a recovery delay TS during which free T1 relaxation occurs, and acquiring balanced steady-state free precession ("bSSFP") recovery data during an acquisition period 218 to obtain a T1 saturation value, which together with the recovery delay TS composes a bSSFP data point 220.

Between or during experiments 210, the MRI controller 33 also receives an EKG signal 230 from the PAC 44. Based on analysis 232 of the EKG signal 230, the MRI controller 33 establishes an estimated heart rate 234. Although for convenience of illustration the EKG signal analysis 232 is shown in FIG. 2 as occurring consecutive with a saturation recovery experiment 210, in certain embodiments the EKG signal analysis 232 may be accomplished concurrently, continuously, and/or in parallel with the saturation recovery experiments 210, for example by utilizing an additional processor within the MRI controller 33.

Based on the estimated heart rate 234, as well as other patient medical data 236 input by an operator (e.g., via the console 13) or obtained via the PAC 44, the MRI controller 33 estimates 240 an expected T1 for the tissue of interest (expected myocardial T1 242). Based on operator selections of scan protocol 250 (e.g., presence or absence of contrast media, and imaging schedule (i.e. systole or diastole imaging)), the MRI controller 33 then chooses 252 a recovery delay TS for the next saturation recovery experiment 210, and also schedules 254 the next saturation pulse 214 to have a negative or positive trigger delay 256 from the next expected R-wave trigger 258. Thus, recovery delays TS and trigger delays 256 are chosen with unprecedented flexibility, based upon at least some or all of an expected T1 of the tissue of interest, expected presence or absence of contrast media, expected or measured heart rate, scanner field strength, and whether imaging is to be done in systole or diastole. Although as discussed with reference to FIG. 2, the selection of recovery delays can be automated within the MRI controller 33, in other aspects of the invention an operator may select the recovery delay based on the factors described above.

Figure 3:
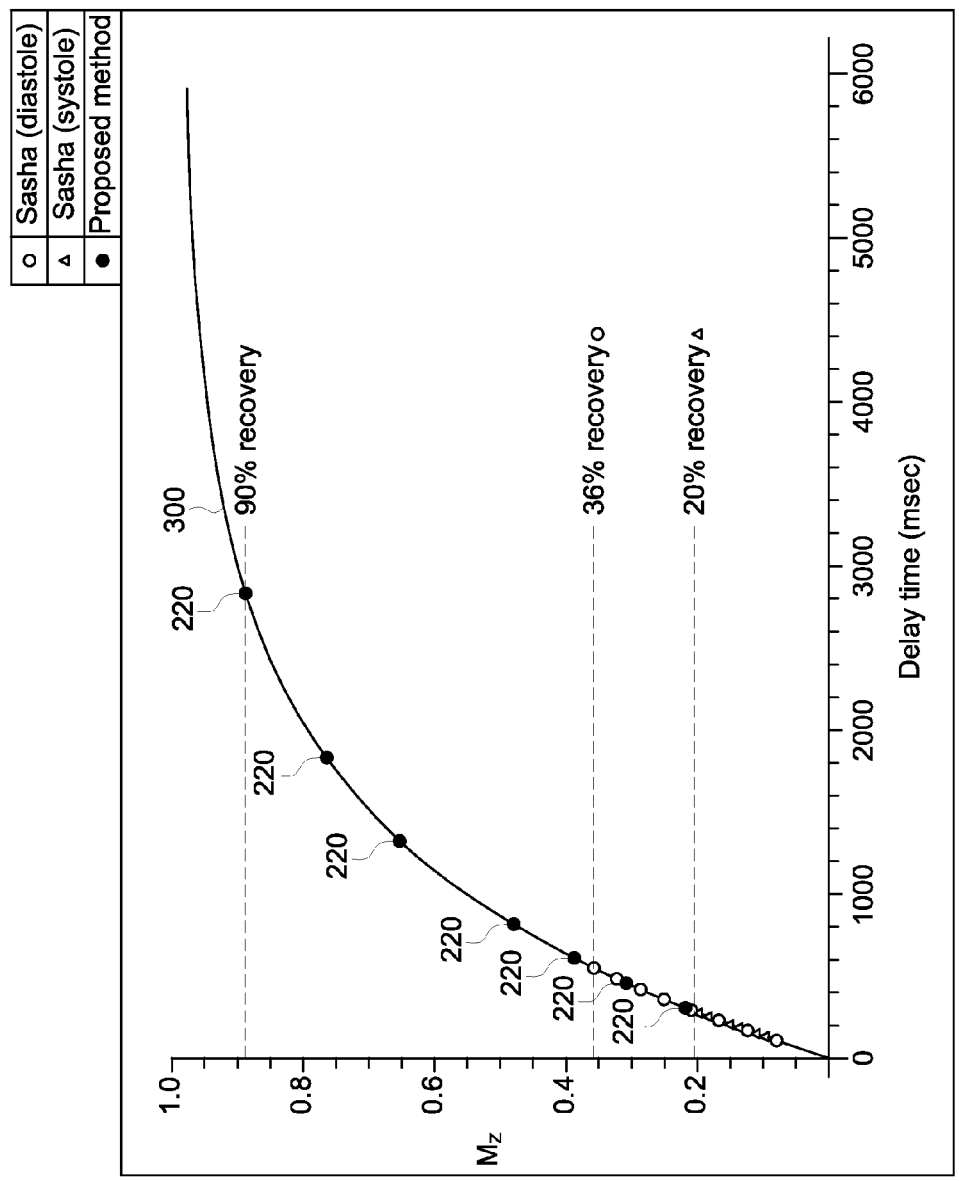
FIG. 3 shows graphically a T1 recovery curve obtainable by the method of FIG. 2.

The pulse sequence 200 includes a sufficient number of repeated experiments 210 to obtain bSSFP data points 220, corresponding to a plurality of recovery delays TS, so as to obtain a good fit of substantially all of a presumed exponential T1 recovery curve 300, e.g., up to about 90% recovery as shown in FIG. 3, or any other portion of the recovery curve 300 that is sufficient to obtain a satisfactory fit; for example in certain embodiments it is desirable to obtain at least about 60% of the curve. One or more of the recovery delays TS may optionally be repeated within the pulse sequence 200. At the conclusion of the pulse sequence 200, the MRI controller 33 may write the bSSFP data points 220, and/or the T1 recovery curve 300, to the computer-readable media 66.

As used herein, the terms "substantially," "generally," and "about" indicate conditions within reasonably achievable manufacturing and assembly tolerances, relative to ideal desired conditions suitable for achieving the functional purpose of a component or assembly. "Adequate points" means at least three points, although a greater number of points will be better for obtaining a good fit. A "good fit" means a fit according to an accepted statistical method, e.g., a non-linear least squares fit or a Legendre fit.

Technical advantages of the inventive method include improved accuracy and precision under most imaging conditions (i.e., it is insensitive to imaging parameters, heart rate and rhythm, and trigger delay) along with unprecedented flexibility in the selection of recovery delays. This will result in superior curve fitting compared to existing methods. A particularly powerful benefit of the inventive method is that flexibility in selecting recovery delays enables automated sampling of the recovery curve. Current cardiac T1 mapping methods require pre-determination of the recovery delays TS, often referred to as a "sampling pattern". Selection of an optimal sampling pattern for those existing methods is an ongoing subject of debate, and can provide an unnecessary source of confusion for users. Automation is not practical or beneficial for other methods because the delays times are limited to a relatively small range of initial recovery delays plus integral multiples of the cardiac cycle added to these initial recovery delays. With this invention, where the recovery delays are nearly unrestricted, two levels of automation are possible.

First, as shown in FIG. 2, the pulse sequence 210 sampling pattern can be determined automatically according to expected myocardial T1 242, pre-contrast vs. post-contrast, desired cardiac phase (i.e., systole or diastole), field strength, estimated heart rate 234, and other patient medical data 236. This way, users need only to prescribe the desired image characteristics.

Second, because heartbeat durations are measured in real time using the EKG signal data 230, the default sampling pattern can also be modified in real time during the scan to optimize sampling based on heart rate variations, according to steps 252 and 254 shown in FIG. 2. "Real time" means generally concurrent with the MRI scan. Real-time heartbeat timing permits the saturation pulse to be placed anywhere in the cardiac cycle (except during data acquisition). This provides improved recovery curve sampling by allowing flexibility in choosing recovery delays and enabling accurate and adaptive measurement of these recovery delays even in the presence of significant heart rate variation or arrhythmia. Thus, another advantage of the proposed method is reliable imaging at high heart rates and in systole. Systolic imaging is often necessary when imaging at high heart rates when diastole is too short for motion-free imaging. It is also desirable for visualizing the myocardium at its thickest, as opposed to diastole where the myocardium is thin. This is of critical importance when imaging the atria or the right side of the heart where the myocardium is often undetectable in diastole (e.g., in arrhythmogenic right ventricular dysplasia/cardiomyopathy (ARVD/C)).

The recovery delays TS, and the associated saturation pulse delays 256, fall into three groups, as shown in FIG. 4. Although FIG. 4 shows a pulse sequence 200 of saturation recovery experiments 210 that are optimized for diastolic imaging, a similar sequence can be optimized for systolic imaging or almost any other cardiac phase.

Figure 4C:
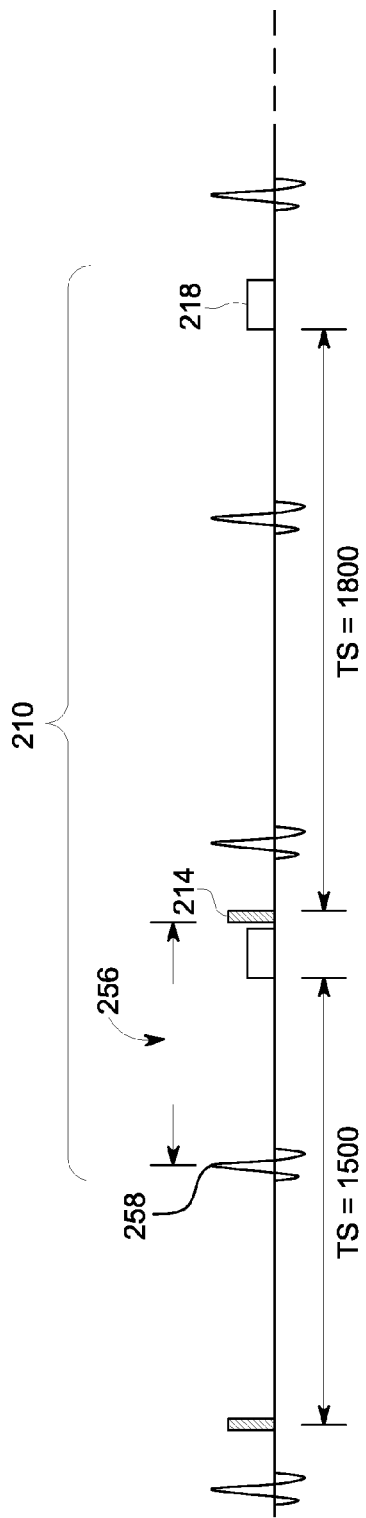

FIG. 4A shows a portion of the pulse sequence 200 in which the saturation recovery experiments 210 have recovery delays within a group of shortest recovery delays TS (less than the trigger delay Tdel), which may be acquired utilizing a small positive trigger delay 256 to place the saturation pulse 214 between an R-wave trigger 258 and the start of the data acquisition period 218. This is a conventional approach for selecting recovery delays. However, the invention admits of choosing recovery delays from the conventional range, and/or from either of two additional groups of recovery delays, which are not conventional, according to FIGS. 4C-4D.

FIG. 4B shows a portion of the exemplary pulse sequence 200 that includes saturation experiments 210 that have recovery delays within a group of moderate recovery delays TS (longer than the trigger delay but shorter than the R-R interval). These saturation experiments place the saturation pulse 214 after the data acquisition period 218 but before the next R-wave trigger 258. Splitting the saturation pulse 214 and the data acquisition period 218 across an R-wave significantly expands the choices for recovery delay.

Figure 4D:
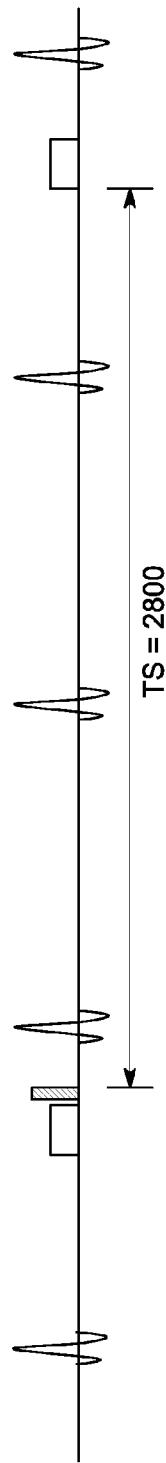

FIGS. 4C-4D show a portion of the exemplary pulse sequence 200 that includes saturation experiments 210 that have recovery delays within a group of longest recovery delays TS (greater than RR). These saturation experiments 210 are acquired across multiple heartbeats, so as to capture an upper portion of the curve 300 shown in FIG. 3. Additionally, one data point 220 may be acquired without imposing a saturation pulse, so as to approximate infinite recovery delay TS.

It should be noted that for the exemplary pulse sequence 200, as shown in FIG. 4, the recovery delays TS are chosen dependent on measured heart rate, according to an expected correlation of heart rate with the sampled points of the T1 recovery curve 300. In order to accurately quantify these longer recovery delays TS, the recovery time may be adapted to changing heart rates by measuring all heartbeats in real time. Thus, the method is insensitive to intra-scan heart rate variations (including arrhythmias).

As a result, aspects of the invention configure the MRI controller for obtaining physiologic data (including the EKG signal data 230) from the PAC 44, possibly obtaining other patient medical data 236, and repeatedly implementing saturation recovery experiments 210 using delay times TS that are chosen based on the physiologic data and the other patient medical data.

In embodiments, a method for mapping T1 in myocardium includes selecting a recovery delay based at least on EKG signal data, imposing a saturation pulse on the myocardium, waiting the recovery delay, and acquiring bSSFP data after the recovery delay. The method may further include fitting a T1 recovery curve to the bSSFP data. The method may include repetitions sufficient to fit at least about 60% of the T1 recovery curve. In certain embodiments, the recovery delay is longer than an R-R interval obtained from the EKG signal data. The saturation pulse may be imposed before an R-wave and the bSSFP data may be acquired after the R-wave. Certain embodiments of the method may include analyzing the EKG signal data to establish at least one of a heart rate or an expected R-wave timing; and/or, analyzing the EKG signal data and other patient medical data to estimate an expected value for myocardial T1. In certain embodiments, the recovery delay is chosen based on EKG signal data as well as at least one of desired cardiac phase for mapping, field strength, or pre-contrast/post-contrast scan protocol. The desired cardiac phase for mapping may be the systolic phase.

Other embodiments provide an MRI system configured for mapping of myocardial T1 in a patient. The inventive MRI system includes a magnet assembly; a physiological acquisition controller configured for connection to the patient; and an MRI controller coupled to the physiological acquisition controller for receiving data that includes EKG signal data, and coupled to the magnet assembly for implementing an MRI pulse sequence. The MRI controller is configured to select a recovery delay based at least on the EKG signal data, impose a saturation pulse on the patient's myocardium via the magnet assembly, wait the recovery delay, and acquire bSSFP data after the recovery delay. The recovery delay may be longer than an R-R interval obtained from the EKG signal data. The saturation pulse may be imposed before an R-wave and the bSSFP data is acquired after the R-wave. The MRI controller may be configured to analyze the EKG signal data to establish at least one of a heart rate or an expected R-wave timing. The MRI controller may be configured to analyze the EKG signal data and other patient medical data to estimate an expected value for myocardial T1. The recovery delay may be chosen based on EKG signal data as well as at least one of desired cardiac phase for mapping, field strength, or pre-contrast/post-contrast scan protocol. For example, the desired cardiac phase for mapping may be the systolic phase. The MRI controller may be configured to fit a T1 recovery curve to the bSSFP data, e.g., after completion of imaging.

In other embodiments, an article of computer-readable media is encoded with at least one bSSFP data point, or a T1 recovery curve, that was obtained according to a process comprising selecting a recovery delay based at least on EKG signal data; imposing a saturation pulse on the myocardium; waiting the recovery delay; and acquiring bSSFP data after the recovery delay. The process may include analyzing the EKG signal data to establish at least one of a heart rate or an expected R-wave timing. The process may include analyzing the EKG signal data and other patient medical data to estimate an expected value for myocardial T1. The recovery delay may be chosen based on EKG signal data as well as at least one of desired cardiac phase for mapping, field strength, or pre-contrast/post-contrast scan protocol. The process may include fitting a T1 recovery curve to the bSSFP data.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice embodiments of the invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of the elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described apparatus, method, and article, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method for mapping T1 in myocardium of a patient, comprising:
choosing a recovery delay from EKG signal data, the EKG signal data being received from a physiological acquisition controller of an MRI system and configured for connection to the patient;
imposing a saturation pulse on the myocardium via an RF coil of the MRI system after an immediately preceding readout obtained by the RF coil and before a next immediate R-wave generated by the patient subsequent to the immediately preceding readout;
waiting the recovery delay;
acquiring bSSFP data from the myocardium via the RF coil after the recovery delay;
mapping T1 of the myocardium based at least in part on the bSSFP data; and
wherein the steps are carried out by an MRI controller coupled to the RF coil and the physiological acquisition controller of the MRI system.

2. The method as claimed in claim 1, further comprising fitting a T1 recovery curve to the bSSFP data.

3. The method as claimed in claim 2, comprising repetitions of the method sufficient to fit at least about 60% of the T1 recovery curve.

4. The method as claimed in claim 1, wherein the recovery delay is longer than an R-R interval obtained from the EKG signal data.

5. The method as claimed in claim 1, wherein the bSSFP data is acquired after the R-wave.

6. The method as claimed in claim 1, further comprising analyzing the EKG signal data to establish at least one of a heart rate or an expected R-wave timing.

7. The method as claimed in claim 6, further comprising analyzing the EKG signal data and other patient medical data to estimate an expected value for myocardial T1.

8. The method as claimed in claim 1, wherein the recovery delay is chosen based on EKG signal data as well as at least one of desired cardiac phase for mapping, field strength, or pre-contrast/post-contrast scan protocol.

9. The method as claimed in claim 8, wherein the desired cardiac phase for mapping is the systolic phase.

10. A process for mapping of myocardial T1 in a patient, the process comprising:
choosing a recovery delay based at least on EKG signal data, the EKG signal data being received from a physiological acquisition controller of an MRI system and configured for connection to the patient;
imposing a saturation pulse on the myocardium via an RF coil of the MRI system after a previously acquired immediately preceding bSSFP data point obtained via the RF coil and before a next immediate R-wave generated by the patient subsequent to the immediately preceding bSSFP data point;
waiting the recovery delay;
acquiring bSSFP data from the myocardium via the RF coil after the recovery delay;
mapping T1 of the myocardium based at least in part on the bSSFP data; and
wherein the steps are carried out by an MRI controller coupled to the RF coil and the physiological acquisition controller of the MRI system.

11. The process as claimed in claim 10, wherein the process further comprises analyzing the EKG signal data to establish at least one of a heart rate or an expected R-wave timing.

12. The process as claimed in claim 11, wherein the process further comprises analyzing the EKG signal data and other patient medical data to estimate an expected value for myocardial T1.

13. The process as claimed in claim 10, wherein the recovery delay is chosen based on EKG signal data as well as at least one of desired cardiac phase for mapping, field strength, or pre-contrast/post-contrast scan protocol.

14. The process as claimed in claim 10, wherein the process further comprises fitting a T1 recovery curve to the bSSFP data.

15. An MRI system configured for mapping of myocardial T1 in a patient, comprising:
a magnet assembly;
a physiological acquisition controller configured for connection to the patient;
an MRI controller coupled to the physiological acquisition controller for receiving data that includes EKG signal data, and coupled to the magnet assembly for implementing an MRI pulse sequence;
wherein the MRI controller is configured to select a recovery delay based at least on the EKG signal data, impose a saturation pulse on the patient's myocardium via the magnet assembly, wait the recovery delay, and acquire bSSFP data after the recovery delay.

16. The apparatus as claimed in claim 15, wherein the recovery delay is longer than an R-R interval obtained from the EKG signal data.

17. The apparatus as claimed in claim 15, wherein the saturation pulse is imposed before an R-wave and the bSSFP data is acquired after the R-wave.

18. The apparatus as claimed in claim 15, wherein the MRI controller is configured to analyze the EKG signal data to establish at least one of a heart rate or an expected R-wave timing.

19. The apparatus as claimed in claim 18, wherein the MRI controller is configured to analyze the EKG signal data and other patient medical data to estimate an expected value for myocardial T1.

20. The apparatus as claimed in claim 15, wherein the recovery delay is chosen based on EKG signal data as well as at least one of desired cardiac phase for mapping, field strength, or pre-contrast/post-contrast scan protocol.

21. The apparatus as claimed in claim 20, wherein the desired cardiac phase for mapping is the systolic phase.

22. The apparatus as claimed in claim 15, wherein the MRI controller is configured to fit a T1 recovery curve to the bSSFP data.

* * * * *